United States Patent [19]

Edwards

[11] 3,941,884
[45] Mar. 2, 1976

[54] PIPERONYL ETHERS HAVING JUVENILE HORMONE MIMETIC ACTIVITY

[75] Inventor: Laroy H. Edwards, Napa, Calif.

[73] Assignee: Chevron Research Company, San Francisco, Calif.

[22] Filed: Jan. 10, 1974

[21] Appl. No.: 432,365

Related U.S. Application Data

[62] Division of Ser. No. 226,963, Feb. 16, 1972, Pat. No. 3,796,726.

[52] U.S. Cl............................ 424/282; 424/DIG. 12
[51] Int. Cl.²............................................ A01N 9/28
[58] Field of Search............................ 424/278, 282

[56] References Cited
UNITED STATES PATENTS

| | | | |
|---|---|---|---|
| 3,563,982 | 2/1971 | Bowers | 424/282 |
| 3,725,551 | 4/1973 | Bowers | 424/282 |
| 3,787,443 | 1/1974 | Erickson | 424/282 |

Primary Examiner—V. D. Turner
Attorney, Agent, or Firm—G. F. Magdeburger; John Stoner, Jr.; Raymond Owyang

[57] ABSTRACT

Compound of the formula

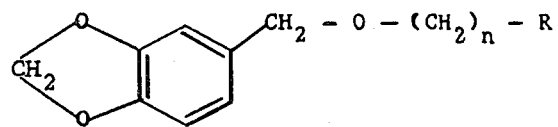

wherein R is hydroxy, halogen of atomic number 9 to 35, vinyl, alkoxy group of 1 to 4 carbon atoms, alkylthio group of 1 to 4 carbon atoms, epoxy group, acyl group or carbamoyl group singly substituted on the nitrogen atom with an alkyl group of 1 to 4 carbon atoms and $n$ is a whole number in the range of 1 to 14, have juvenile hormone mimetic activity.

19 Claims, No Drawings

PIPERONYL ETHERS HAVING JUVENILE HORMONE MIMETIC ACTIVITY

This is a division of application Ser. No. 226,963, filed Feb. 16, 1972, now U.S. Pat. No. 3,796,726.

BACKGROUND OF THE INVENTION

1. Field

The present invention is concerned with piperonyl ethers that have juvenile hormone mimetic activity. More particularly, it is concerned with straight chain ω-monounsaturated alkenyl, ω-haloalkyl, ω-hydroxyalkyl, ω-epoxyalkyl, ω-alkoxyalkyl, ω-alkylthioalkyl, ω-acylalkyl and ω-carbamoylalkyl piperonyl ethers.

2. Prior Art

Juvenile hormone is a methyl ester of a multiply unsaturated branched chain acid. This branched chain group is made up of isoprene units characteristic of many natural products. The resulting complex structure is difficult to synthesize and is, therefore, not readily available for insect control.

Compounds which function as juvenile hormone insecticides act in a different manner on insects than presently used insecticides. Compounds having juvenile hormone mimetic activity exert a disrupting influence upon the normal development of the insects. These compounds interrupt the normal metamorphosis of the pest insects and result in the formation of members of the treated species which develop abnormally and are nonviable or sterile. This ultimately leads, indirectly at least, to the destruction of the insect population.

DESCRIPTION OF THE INVENTION

The compounds of the present invention, in general, possess juvenile hormone mimetic activity. The compounds are straight chain piperonyl ethers having the following structure (I)

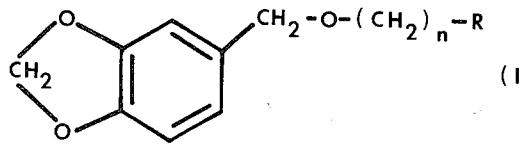

(I)

wherein R is —OH, halogen of atomic number 9 to 35 (fluorine, chlorine or bromine), vinyl, alkoxy of 1 to 4 carbon atoms, alkylthio of 1 to 4 carbon atoms, epoxy, acyl of 1 to 5 carbon atoms, carbamoyl singly substituted on the nitrogen atom with alkyl groups of 1 to 4 carbon atoms and n is a whole number of 1 to 14.

Preferably R is hydroxy, chlorine, bromine, vinyl, alkoxy of 1 to 2 carbon atoms, alkylthio of 1 to 2 carbon atoms, epoxy, saturated acyl of 2 carbon atoms or carbamoyl singly substituted on the nitrogen with a methyl group.

n is preferably a whole number in the range of 2 to 14, more preferably 2 to 12 and most preferably 6 to 12.

The acyl groups may be represented by the structure (II)

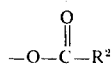  (II)

wherein $R^2$ is alkyl of 1 to 4 carbon atoms, preferably methyl or cyclopropyl. The carbamoyl group may be represented structurally as

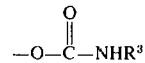  (III)

wherein $R^3$ is alkyl of 1 to 4 carbon atoms, preferably methyl.

Still more preferably R is bromine, vinyl or methoxy and n has a value of 9 to 10.

Representative compounds of the present invention include the following: 2-hydroxyethyl piperonyl ether, 4-hydroxybutyl piperonyl ether, 8-hydroxyoctyl piperonyl ether, 2-bromoethyl piperonyl ether, 3-bromopropyl piperonyl ether, 4-bromobutyl piperonyl ether, 5-bromopentyl piperonyl ether, 7-bromoheptyl piperonyl ether, 11-bromoundecyl piperonyl ether, 13-bromotridecyl piperonyl ether, 14-bromotetradecyl piperonyl ether, 12-chlorododecyl piperonyl ether, 9-fluorononyl piperonyl ether, 2-fluoroethyl piperonyl ether, 2-fluoromethyl piperonyl ether.

Allyl piperonyl ether, 3-butenyl piperonyl ether, 4-pentenyl piperonyl ether, 6-heptenyl piperonyl ether, 10-undecenyl piperonyl ether, 11-dodecenyl piperonyl ether, 12-tridecenyl piperonyl ether.

2-Methoxyethyl piperonyl ether, 2-propoxyethyl piperonyl ether, 3-propoxypropyl piperonyl ether, 4-ethoxybutyl piperonyl ether, 5-ethoxypentyl piperonyl ether, 7-methoxyheptyl piperonyl ether, 11-methoxyundecyl piperonyl ether, 12-methoxy dodecyl piperonyl ether, 13-methoxytridecyl piperonyl ether, 9-ethoxynonyl piperonyl ether, 10-ethoxydecyl piperonyl ether, 10-butoxydecyl piperonyl ether, 11-ethoxyundecyl piperonyl ether, 8-propoxyoctyl piperonyl ether, 9-propoxynonyl piperonyl ether, 10-propoxydecyl piperonyl ether, 11-propoxyundecyl piperonyl ether, 7-butoxyheptyl piperonyl ether, 9-butoxynonyl piperonyl ether, 10-butoxydecyl piperonyl ether.

8-Thianonyl piperonyl ether, 9-thiadecyl piperonyl ether, 10-thiaundecyl piperonyl ether, 12-thiatridecyl piperonyl ether, 8-thiadecyl piperonyl ether, 8-thiaundecyl piperonyl ether, 8-thiadodecyl piperonyl ether, 2-thiapropyl piperonyl ether, 3-thiapentyl piperonyl ether, 3-thiahexyl piperonyl ether.

3,4-Epoxybutyl piperonyl ether, 4,5-epoxypentyl piperonyl ether, 5,6-epoxyhexyl piperonyl ether, 6,7-epoxyheptyl piperonyl ether, 9,10-epoxydecyl piperonyl ether, 10,11-epoxyundecyl piperonyl ether, 11,12-epoxydodecyl piperonyl ether, 12,13-epoxytridecyl piperonyl ether, 13,14-epoxytetradecyl piperonyl ether.

8-Piperonyloxyoctyl acetate, 7-piperonyloxyheptyl acetate, 11-piperonyloxyundecyl acetate, 12-piperonyloxydodecyl acetate, 9-piperonyloxynonyl propionate, 10-piperonyloxydecyl propionate, 11-piperonyloxyundecyl propionate, 9-piperonyloxynonyl butyrate, 10-piperonyloxydecyl butyrate, 8-piperonyloxyoctyl butyrate, 9-piperonyloxynonyl cyclopropanecarboxylate, 10-piperonyloxydecyl cyclopropanecarboxylate, 8-piperonyloxyoctyl cyclopropanecarboxylate, 8-piperonyloxyoctyl-N-methyl carbamate, 11-piperonyloxyundecyl-N-methyl carbamate, 12-piperonyloxydodecyl-N-methyl carbamate, 13-piperonyloxytridecyl-N-methyl carbamate The ω-haloalkyl piperonyl ethers of this invention are prepared by the reaction of sodium piperonoxide and an α,ω-dibromoalkane as follows:

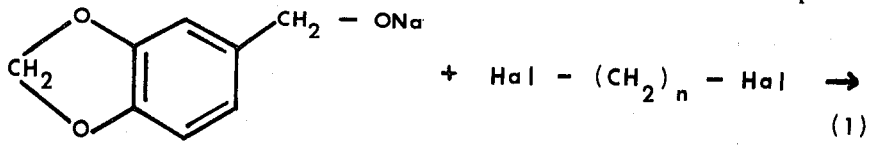

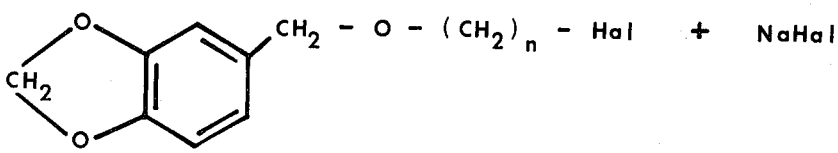

wherein $n$ has the same meaning as before and Hal represents halogen of atomic number 9 to 35. Other alkali metal salts may be used, e.g., potassium, lithium, etc.

This reaction (1) is a variation of the well known Williamson ether synthesis. The dihalide in an equal molar amount is simply added to the solvent (e.g., dimethoxy ethane, liquid ammonia, tetrahydrofuran, dioxane, etc.) containing the piperonyl salt which is then heated at temperatures in the range of 50° to 150°C. for a period of time sufficient to carry the reaction to completion about 6 to 24 hours. This reaction is conveniently catalyzed by a small amount of iodine. After water washing to remove the by-product salts, crude product is obtained by evaporation or distillation of the solvent. This crude material may be used as such or it may be purified by chromatography.

The alkali metal salts of piperonol are readily prepared by the reaction of piperonol with an equal molar amount of sodium hydride, potassium amide, n-butyl lithium, etc. in an appropriate solvent such as dimethoxy ethane, liquid ammonia, tetrahydrofuran, dioxane and the like. This reaction is carried out at low temperatures, below about 50°C. The alkali metal salt is usually prepared in situ and used in the subsequent reaction with an α,ω-dihaloalkane without isolation or purification.

The ω-unsaturated alkenyl piperonyl ethers of this invention may be prepared by dehydrohalogenation of ω-haloalkyl piperonyl ethers as illustrated by the reaction below, wherein the halogen is represented as bromine:

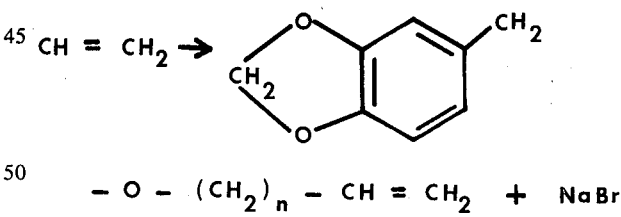

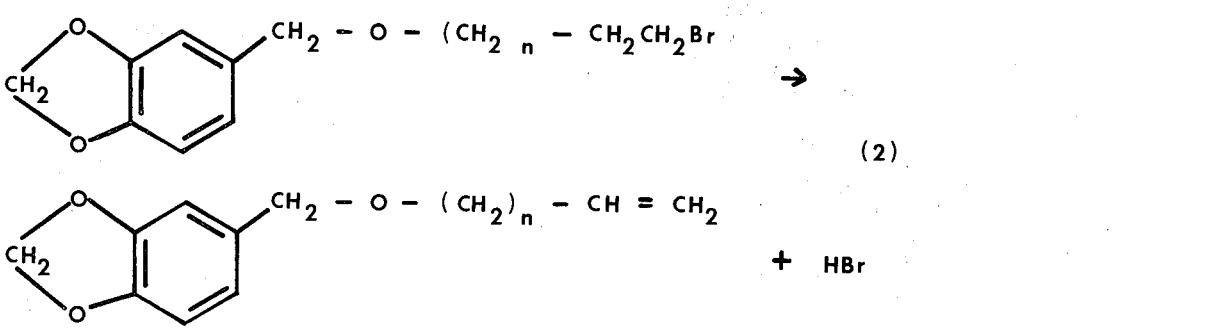

wherein $n$ is as defined previously.

In this reaction (2) the ω-haloalkyl piperonyl ether is heated with an excess of a strong base in an inert nonaqueous solvent. Solvents suitable for this reaction are preferably high boiling and include dimethoxyethane, dioxane, diethyleneglycol, monoethyl ether of diethyleneglycol and the like. Strong bases for this reaction include the alkali metal hydroxides, e.g. sodium hydroxide, potassium hydroxide, etc. The reaction is carried out at temperatures in excess of 50°C., preferably at the reflux temperature of the solvent. Reaction times for completion depend on the temperature but are generally in the range of 4 to 24 hours. The crude product is obtained by evaporating or distilling off the solvent after it has been washed to remove by-product salts.

The ω-unsaturated alkenyl piperonyl ethers of this invention may also be prepared by the reaction of a terminally unsaturated primary alcohol and piperonyl halide as follows (the halogen is represented by bromine):

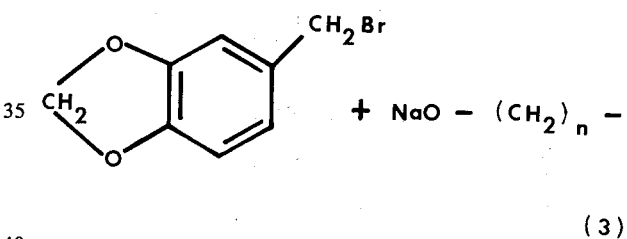

This reaction is essentially the same as process (1) described above for the preparation of ω-haloalkyl piperonyl ethers.

The ω-alkoxyalkyl piperonyl ethers and the ω-alkylthioalkyl piperonyl ethers are prepared from the corresponding ω-haloalkyl piperonyl ethers as follows:

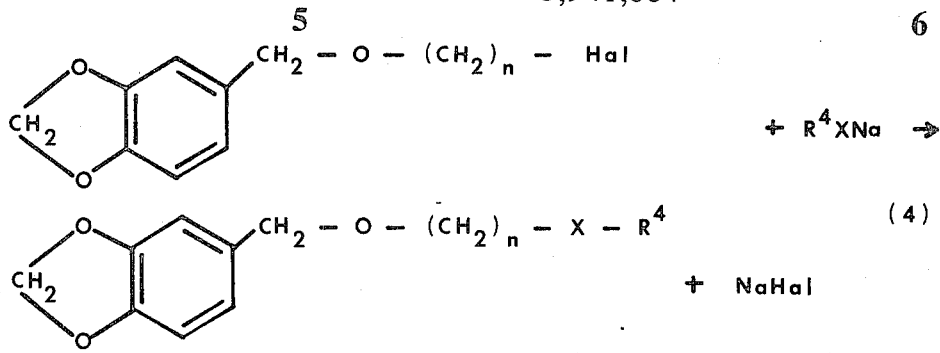

This reaction is essentially the same as reaction (1) described above for the preparation of ω-haloalkyl piperonyl ethers and is carried out in substantially the same manner.

The ω-epoxyalkyl piperonyl ethers of this invention are prepared by epoxidizing the terminally unsaturated alkenyl piperonyl ethers, as follows:

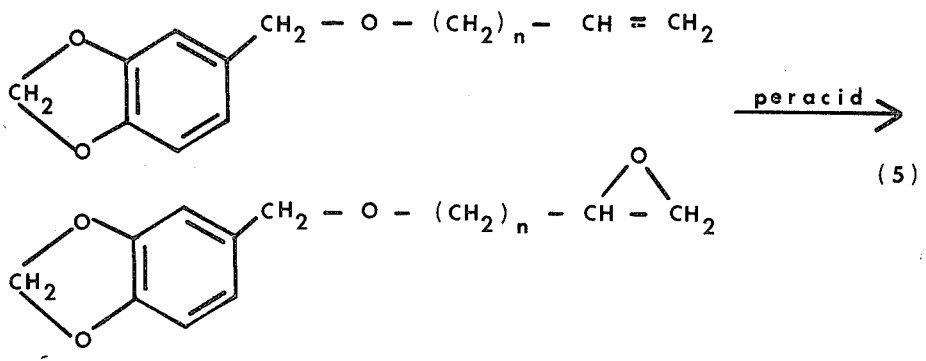

wherein $n$ has the same meaning as before.

Epoxidations are well known reactions of olefins and are effected by contacting the olefin with an epoxidizing agent such as perbenzoic acid, m-chloroperbenzoic acid, and peracetic acid. The reaction is usually carried out in solvents such as chloroform, acetic acid and diethyl ether, at temperatures below about 25°C., preferably 0°–10°C. The reactants are mixed slowly and kept in contact at these low temperatures for periods of time ranging from 2 hours to 2 or more days. The product is obtained by first washing out the acid by-products with a dilute basic solution, and then removing the organic solvent by evaporation or distillation. The crude product obtained in this way may be used as such or it may be purified by chromatography.

The ω-hydroxyalkyl piperonyl ethers are prepared by the reaction of piperonyl bromide and a sodium ω-hydroxyalkoxide as follows:

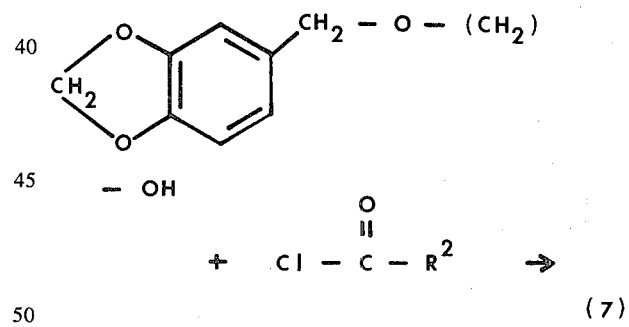

This reaction is carried out in a manner substantially the same as that described above for reaction (3).

The ω-acylalkyl piperonyl ethers and the ω-carbamoylalkyl piperonyl ethers are prepared by reacting ω-hydroxyalkyl piperonyl ether with a suitable acyl-chloride or alkyl isocyanate, respectively, according to the following equations (7) and (8):

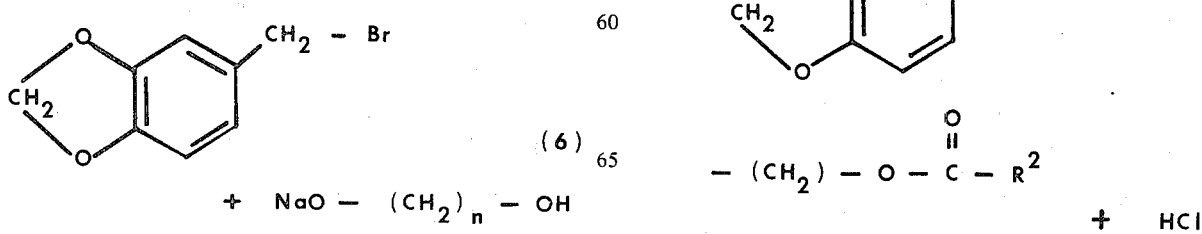

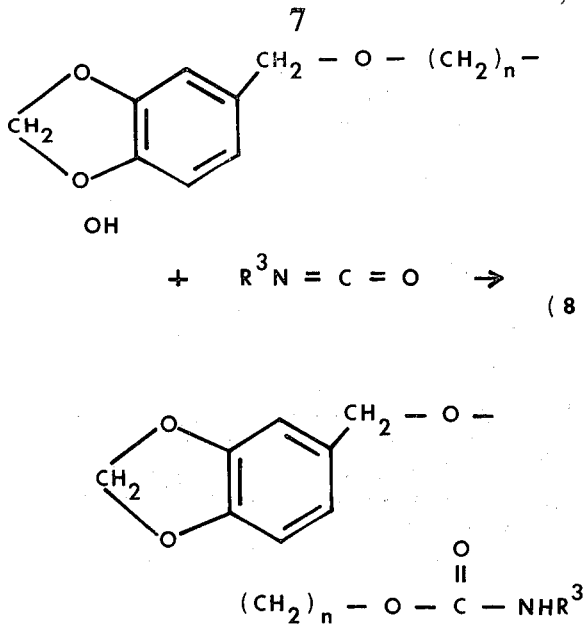

The above reactions are, of course, well known acylation and carbamoylation reactions. The ω-acylalkyl piperonyl ethers may also be prepared by reacting the ω-hydroxyalkyl piperonyl ether with an anhydride such as acetic anhydride. This reaction is also well known.

The compounds of the present invention may be more fully understood by reference to the following examples.

EXAMPLE 1

Preparation of 8-bromooctyl piperonyl ether

Piperonol, 15.2 g. (0.1 mole), was dissolved in 200 ml. of dimethoxyethane. To this solution there was added 4.8 g. (0.1 mole) of sodium hydride. The resulting mixture was refluxed for 30 minutes after which 27.2 g. (0.1 mole) of 1,8-dibromooctane and a crystal of iodine were added. This mixture was then refluxed for 24 hours. At the end of this time, the mixture was cooled and mixed with an equal amount of water. Then a like amount of dichloromethane was added and the two layers were separated. The organic layer was dried and evaporated. The crude product obtained in this way was purified by passing through a silica gel chromatography column using a 5% ether in hexane eluent. In this way there was obtained 13 g. of oily 8-bromooctyl piperonyl ether. The NMR spectra was consistent with the assigned structure. An infrared spectra had strong adsorptions at 3.4, 3.5, 6.7, 6.95, 8.0, 9.1, 9.6, 10.7 and 12.3 microns. Analysis was as follows:

|      | Calculated | Found |
|------|------------|-------|
| Br % | 23.3       | 23.3  |

EXAMPLE 2

Preparation of 7-octenyl piperonyl ether

A crude 8-bromooctyl piperonyl bromide was prepared by refluxing 15.2 g. (0.1 mole) of piperonol, 27.2 g. (0.1 mole) of 1,8-dibromooctane and 13.8 g. (0.1 mole) of potassium carbonate in 200 ml. of acetone for 36 hours. At the end of this time the mixture was filtered and evaporated to dryness. To this crude product there was added 200 ml. of dimethoxy ethane and 11.2 g. (0.2 mole) of potassium hydroxide. The resulting mixture was heated at reflux for 24 hours, after which the material was cooled, filtered and evaporated to give crude 7-octenyl piperonyl ether. This product was purified by passing it through a silica gel chromatography column using petroleum ether as the eluent. The purified 7-octenyl piperonyl ether was an oil and weighed 5 g. NMR spectra was consistent with the assigned structure. Infrared spectra had strong adsorption bands at 3.4, 3.5, 6.1, 6.7, 6.95, 8.0, 9.1, 9.6, 10,6, 10.9 and 12.3 microns. Analysis was as follows:

|     | Calculated | Found |
|-----|------------|-------|
| C % | 73.3       | 74.9  |
| H % | 8.4        | 8.5   |

EXAMPLE 3

Preparation of 8-methoxyoctyl piperonyl ether 8-bromopiperonyl ether, 19.0 g. (0.55 mole) and 5.6 g. (0.1 mole) of potassium hydroxide were refluxed in 150 ml. of methanol for 2 hours. After cooling, the reaction mixture was filtered and the filtrate evaporated to give a residue which was chromatographed through a silica gel column using a 5% ether in hexane eluent to obtain a first fraction and a 20% ether in hexane eluent to obtain a second fraction. The first fraction was evaporated to give 3 g. of 7-octenyl piperonyl ether, the second fraction was evaporated to give 8 g. of oily, 8-methoxyoctyl piperonyl ether. The NMR spectra was consistent with the assigned structure. An infrared spectra had stong adsorption peaks at 3.4, 3.5, 6.7, 6.95, 8.0, 8.9–9.1, 9.6, 10.6 and 12.3 microns. Analysis was as follows:

|     | Calculated | Found |
|-----|------------|-------|
| C % | 69.4       | 70.5  |
| H % | 8.8        | 9.0   |

EXAMPLE 4

Preparation of 10-undecenyl piperonyl ether

A. Piperonyl bromide

Piperonol, 30.4 g. (0.2 mole) was added in small portions to 200 ml. of 48% hydrobromic acid at 0°C. When all had been added, the reaction mixture was diluted with 200 ml. of water and stirred for an additional 30 minutes. Then 200 ml. of dichloromethane was added. The layers were separated, the organic layer was washed with water and dried over magnesium sulfate. The solvent was removed by evaporation under reduced pressure to give 38.5 g. of piperonyl bromide.

B. 10-undecenol-1

To a mixture of 7.6 g. (0.2 mole) of lithium aluminum hydride in 100 ml. of ether, there was added over a period of 3 hours, 36.8 g. (0.2 mole) of 10 undecenoic acid dissolved in 100 ml. of ether. When all was added the resulting mixture was refluxed for 1½ hours. The resulting mixture was then added to 200 ml. of 3N hydrochloric acid. The ether layer was separated, washed with aqueous sodium bicarbonate, and dried over magnesium sulfate. The solvent was removed under vacuum to give a crude product which was washed with aqueous potassium carbonate, dissolved in hexane and dried again. Evaporation of the hexane gave 34 g. of 10-undecenol-1.

C. 10-undecenyl piperonyl ether

Sodium hydride, 4.8 g. (0.1 mole) was added to a stirred solution of 7.0 g. (0.1 mole) of 10-undecenol-1 in 100 ml. of hexane. The resulting mixture was refluxed for 1½ hours. At the end of this time, 21.5 g. (0.1 mole) of piperonyl bromide dissolved in 200 ml. of hexane was added and refluxing was continued for 18 hours. Then the reaction mixture was added to 300 ml. of water. The organic layer was separated and dried. After evaporation of the solvent the crude product obtained thereby was passed through a silica gel chromatographic column using a 10% ether in hexane eluent. The purified 11-undecenyl piperonyl ether weighed 17 g. The infrared spectra had strong adsorption bands at 3.4, 3.5, 6.1, 6.7, 6.95, 8.0, 9.1, 9.6, 10.7, 11.0 and 12.3 microns.

EXAMPLE 5

Preparation of 10, 11-epoxyundecenyl piperonyl ether

To a solution of 11.0 g. (0.036 mole) of 10-undecenyl piperonyl ether and 5.0 g. (0.036 mole) of sodium dihydrogen phosphate monohydrate in 100 ml. of dichloromethane, was added 7.6 g. (0.036 mole) of m-chloroperbenzoic and dissolved in 200 ml. of dichloromethane. After stirring at ambient temperature for 24 hours, the mixture was filtered and washed with an aqueous sodium bicarbonate solution. After drying the dichloromethane solvent was removed by evaporation. The crude product obtained in this way was purified by passing through a silica gel chromatographic column using first a 5% ether in hexane eluent and then a 50% ether in hexane eluent to recover the 10,11-epoxyundecenyl piperonyl ether which weighed 5 g. An infrared spectra had strong adsorption peaks at 3.4, 3.5, 6.7, 6.95, 7.9–8.0, 9.1, 9.6, 10.8 and 12.4 microns.

EXAMPLE 6

Preparation of 13-thiatetradecyl piperonyl ether

Methyl mercaptan, 1.6 g. (0.032 mole) was bubbled into a solution of 13.0 g. (0.032 mole) of 12-bromododecyl piperonyl ether, and 5.6 g. (0.1 mole) of potassium hydroxide in 150 ml. of dimethoxyethane. When all had been added the resulting mixture was heated at reflux for 3 hours. After cooling and filtering, the solvent was removed by evaporation. The crude product was then dissoved in hexane and filtered. The filtrate was evaporated to give 8.5 g. of oily product. The NMR spectra was consistent with the assigned structure. The infrared spectra had strong adsorption peaks at 3.4, 3.5, 6.7, 6.95, 8.0, 9.0, 9.6, 10.6 and 12.2 microns. Analysis was as follows:

|  | Calculated | Found |
|---|---|---|
| C % | 68.7 | 69.5 |
| H % | 9.3 | 9.7 |

Other compounds were prepared from appropriate starting materials using the procedures described above. These compounds are given in Table I.

TABLE I

| Ex. No. | Compound | Melting Point °C. | Calculated C | Calculated H | Calculated Br | Found C | Found H | Found Br |
|---|---|---|---|---|---|---|---|---|
| 7 | 6-bromohexyl piperonyl ether | Oil | — | — | 25.4 | — | — | 25.5 |
| 8 | 9-bromononyl piperonyl ether | Oil | — | — | 22.4 | — | — | 24.3 |
| 9 | 10-bromodecyl piperonyl ether | Oil | — | — | 21.6 | — | — | 20.4 |
| 10 | 12-bromododecyl piperonyl ether | 25–27 | — | — | 20.0 | — | — | 19.1 |
| 11 | 5-hexenyl piperonyl ether | Oil | 71.8 | 7.7 | — | 64.3 | 7.3 | — |
| 12 | 9-decenyl piperonyl ether | Oil | 74.5 | 9.0 | — | 72.3 | 9.3 | — |
| 13 | 11-dodecenyl piperonyl ether | Oil | — | — | — | — | — | — |
| 14 | 6-methoxyhexyl piperonyl ether | Oil | 67.7 | 8.3 | — | 69.2 | 8.7 | — |
| 15 | 9-methoxynonyl piperonyl ether | Oil | 70.2 | 9.1 | — | 72.0 | 9.0 | — |
| 16 | 10-methoxydecyl piperonyl ether | Oil | 70.8 | 9.3 | — | 69.6 | 9.3 | — |
| 17 | 12-ethoxydodecyl piperonyl ether | Oil | — | — | — | — | — | — |
| 18 | 11-methoxyundecyl piperonyl ether | Oil | 71.4 | 9.5 | — | 71.9 | 9.6 | — |
| 19 | 11-bromoundecyl piperonyl ether | Oil | — | — | 20.8 | — | — | 20.6 |
| 20 | 9-chlorononyl piperonyl ether | Oil | — | — | 11.4* | — | — | 11.2* |

| Ex. No. | Compound | Melting Point °C | Calculated C | Calculated H | Calculated N | Found C | Found H | Found N |
|---|---|---|---|---|---|---|---|---|
| 21 | 9-hydroxynonyl piperonyl ether | 25 | 69.4 | 8.8 |  | 68.5 | 9.2 |  |
| 22 | 10-hydroxydecyl piperonyl ether | 28 | 70.2 | 9.1 |  | 71.5 | 9.4 |  |
| 23 | 9-piperonyloxynonyl acetate | 31–32 | 67.9 | 8.3 |  | 68.6 | 8.4 |  |
| 24 | 10-piperonyloxydecyl acetate | Oil | 68.6 | 8.6 |  | 68.7 | 8.8 |  |
| 25 | 9-piperonyloxynonyl N-methylcarbamate | 50–51 | 65.0 | 8.3 | 4.0 | 65.9 | 8.2 | 4.1 |
| 26 | 10-piperonyloxydecyl N-methyl carbamate | 66–68 | 65.7 | 8.5 | 3.8 | 66.6 | 8.7 | 3.7 |
| 27 | 12-piperonyloxydodecyl acetate | 26–27 | 70.0 | 9.0 |  | 69.2 | 8.7 |  |
| 28 | 9-piperonyloxynonyl cyclopropanecarboxylate | Oil | 69.5 | 8.2 |  | 65.6 | 7.9 |  |
| 29 | 10-piperonyloxydecyl cyclopropanecarboxylate | Oil | 70.2 | 8.52 |  | 69.2 | 8.3 |  |
| 30 | 12-piperonyloxydodecyl cyclopropanecarboxylate | 26 | 71.2 | 8.92 |  | 70.3 | 8.8 |  |
| 31 | 12-hydroxydodecylpiperonyl ether | 33 | 71.4 | 9.23 |  | 72.4 | 9.6 |  |
| 32 | 10-piperonyloxydecyl propionate | Oil | 69.3 | 8.8 |  | 67.8 | 8.8 |  |
| 33 | 10-piperonyloxydecyl butyrate | Oil | 70.0 | 9.0 |  | 67.4 | 8.7 |  |

*chlorine

The compounds of the present invention are useful as insecticides, particularly as juvenile hormone mimetic insecticides; that is they inhibit the normal growth pattern of certain insects thereby limiting reproduction of these insects.

The compounds of the present invention were tested as juvenile hormone mimetic insecticides against the following insects: Yellow mealworm (Tenebrio molitor), Cabbage looper (Trichoplusia ni) and Kissing bug (Rhodnius prolixus).

The test procedures were substantially as follows:

For the Yellow mealworm test an acetone solution containing a certain concentration in micrograms of the test compound in 5 microliters of solution was topically applied to the abdomens of the mealworm pupae which were less than 48 hours old. Usually 10 pupae were so treated. The treated pupae were placed in a Petri dish and placed in an incubator at 27°C. in darkness until they emerged (or tried to emerge) about one week after treatment. A count was made of the dead. The live specimens were examined under a microscope for juvenilization, i.e. retention of pupa characteristics in the adult. The degree of juvenilization was scored by the method of W. S. Bowers and M. J. Thompson (Science 142, 1469–70 (1963)). In this method of scoring:

0 = normal appearing adult
0.5 = essentially normal appearing adult, slight trace of "gin" traps
1 = slight retention of pupa characteristics
4 = supernumery of second pupa, maximum juvenilization.

The results are reported in Table II.

For the Cabbage looper, an acetone solution containing a certain concentration in micrograms of the test compound in 5 microliters of solution was applied topically to the entire length of the body of a late fifth stage larva. Normally 10 larvae were treated per test. The treated larvae were then fed until they pupated. The pupae were examined under a microscope, checking for any retention of larvae characteristics in the pupae (juvenilization). Juvenilization as well as mortality readings were made. The pupae were incubated until the adult emerged. Mortality of the adults was determined. The degree of juvenilization was measured based on the following:

0 = normal appearing pupa
1 = ½ larva - ½ pupa; no prolegs; pupoid thorax
2 = ½ larva - ½ pupa; prolegs; pupoid thorax
3 = supernumery larva The results are reported in Table II.

For the Kissing bug test a certain amount in micrograms of test material in 5 microliters of acetone was applied to the abdomens of later fifth stage nymphs, 24 hours after they had a blood meal. About two weeks later the adult was observed under a microscope for signs of juvenilization. The degree of juvenilization was scored by the method of V. B. Wigglesworth (J. Insect Physiology 2, 73 (1958)). This method has a 19 point score for rating the nymph characteristics:

0 = normal adult — no effect
1 – 9 = adult with nymph like characteristics
11 – 18 = nymph with some adult characteristics
19 = supernumery nymph (sixth stage).

Percent control, based on larva, pupa and adult insect mortality readings at each stage are reported in Table II.

TABLE II

| Compound of Ex. No. | Yellow Mealworm Conc. μg/insect | Juvenilization % (Degree) | % Control | Cabbage Looper Conc. μg/insect | Juvenilization % (Degree) | % Control | Kissing Bug Conc. μg/insect | Juvenilization % (Degree) | % Control |
|---|---|---|---|---|---|---|---|---|---|
| 1 | 50 | 50 (2.6) | 100 | 100 | 30 (1) | 50 | 3 | 100 (14) | 100 |
| 2 | 10 | 90 (2.9) | 100 | 100 | 0 | 30 | 10 | 100 (19) | 100 |
| 3 | 10 | 100 (3.5) | 100 | 100 | 0 | 0 | 3 | 70 (9.4) | 100 |
| 4 | 100 | 100 (2.4) | 100 | 100 | 70 (2.9) | 100 | 1 | 80 (16) | 100 |
| 5 | 250 | 40 (0.5) | 0 | 250 | — | 30 | 10 | 60 (7) | 100 |
| 6 | 100 | 100 (1.8) | 100 | 100 | 10 (1) | 20 | 100 | 100 (19) | 100 |
| 7 | 100 | 20 (0.5) | 0 | 100 | 0 | 0 | 10 | 100 (17) | 100 |
| 8 | 30 | 100 (3.5) | 100 | 100 | 10 (1) | 50 | 1 | 100 (15) | 100 |
| 9 | 100 | 70 (1.4) | 30 | 100 | 0 | 0 | 1 | 100 (15) | 100 |
| 10 | 100 | 40 (0.5) | 0 | 100 | 0 | 0 | 100 | 100 (19) | 100 |
| 11 | 10 | 100 (2.1) | 100 | 100 | 0 | 20 | — | — | — |
| 12 | 100 | 100 (4) | 100 | 100 | 40 (1) | 60 | 3 | 100 (19) | 100 |
| 13 | 100 | 100 (4) | 100 | 100 | 10 (1) | 10 | 10 | 100 (19) | 100 |
| 14 | 10 | 100 (4) | 100 | 100 | 0 | 10 | — | — | — |
| 15 | 10 | 90 (1.8) | 100 | 100 | 0 | 0 | 3 | 100 (14.1) | 100 |
| 16 | 30 | 100 (2.7) | 100 | 100 | 10 (1) | 30 | 100 | 100 (19) | 100 |
| 17 | 100 | 100 (4) | 100 | 100 | 0 | 0 | 100 | 100 (19) | 100 |
| 18 | 10 | 0 | 0 | 100 | 0 | 0 | 10 | 100 (19) | 100 |
| 19 | 10 | 0 | 0 | 100 | 20 (2) | 20 | 10 | 100 (19) | 100 |
| 20 | 10 | 0 | 0 | 100 | 0 | 0 | — | — | — |
| 21 | 10 | 0 | 0 | 100 | 0 | 0 | — | — — | |
| 22 | 10 | 0 | 0 | 100 | 0 | 0 | — | — | — |
| 23 | 10 | 0 | 0 | 100 | 0 | 20 | — | — | — |
| 24 | 10 | 0 | 0 | 100 | 0 | 0 | — | — | — |
| 25 | 10 | 0 | 0 | — | — | — | — | — | — |

The acyl derivatives (wherein R = acyl) of the compounds of the invention, particularly those of structure II wherein $R^2$ is methyl or cyclopropyl, are also effective as ovicides. For example, 10-piperonyloxydecyl cyclopropanecarboxylate and 10-piperonyloxydecyl acetate, were found to possess ovicidal activity against eggs of the two-spotted spider mite (*Tetranychus urtica Koch*).

When used as an insecticide the compounds may be applied in either liquid or solid formulations to the insects, their environment or hosts susceptible to insect attack. For example, they may be sprayed or otherwise applied directly to plants or soil so as to effect control of insects coming into contact therewith.

Formulations of the compounds of this invention will comprise a toxic amount of one or more of the compounds and a biologically inert carrier. Usually they will also contain a wetting agent. Solid carriers such as clay, talc, sawdust and the like may be used in such formulations. Liquid diluents which may be used with these compounds include water and aromatic solvents. In addition these formulations may contain other compatible pesticides, fillers, stabilizers, attractants and the like.

The concentration of the active ingredient to be used with inert carriers, either solid or liquid carriers, will be dependent upon many factors, such as the particular compound which is used, the carrier in or upon which it is incorporated, the method and conditions of application, the insect species to be controlled, etc., the proper consideration of these factors being within the skill of those versed in the art. In general, the toxic ingredients of this invention will be effective in concentrations from about 0.0001 percent by weight to as high as 50 percent by weight or higher. Economically, of course, it is desirable to use lower concentrations of this active ingredient. Thus, it is usually desirable to use less than 20 percent by weight of the active ingredient in a particular composition.

The terms "insecticide" and "insect" as used herein refer to their broad and commonly understood usage rather than to those creatures which in the strict biological sense are classified as insects. Thus, the term "insect" is used not only to include small invertebrate animals belonging to the class Insecta but also to other related classes of arthropods whose members are segmented invertebrates having more or fewer than six legs, such as spiders, mites, ticks, centipedes, worms and the like.

As will be evident to those skilled in the art, various modifications on this invention can be made or followed, in the light of the foregoing disclosure and discussion, without departing from the spirit or scope of the disclosure or from the scope of the following claims.

I claim:

1. A method for killing insects selected from the group consisting of Tenebrio molitor, Trichoplusia ni and Rhodnius Prolixus which comprises contacting the insects with a metamorphosis-inhibiting amount of a compound of the formula

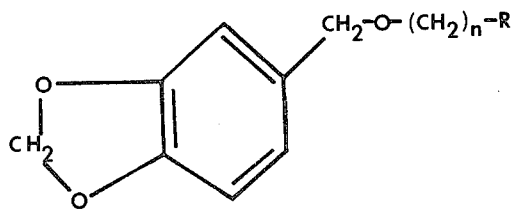

where R is hydroxy, halogen of atomic number 9 to 35, vinyl, alkoxy of 1 to 4 carbon atoms, alkylthio of 1 to 4 carbon atoms, epoxy, acyclic carboxylic acyl of 1 to 5 carbon atoms or carbamoyl singly substituted on the nitrogen atom with alkyl of 1 to 4 carbon atoms and $n$ is 1 to 14.

2. A method in accordance with claim 1 wherein $n$ is 2 to 14.

3. A method in accordance with claim 1 wherein n is 6 to 12.

4. A method in accordance with claim 1 wherein R is hydroxy, chlorine, bromine, vinyl, alkoxy of 1 to 2 carbon atoms, alkylthio of 1 to 2 carbon atoms, epoxy, acyclic carboxylic acyl of 2 carbon atoms or carbamoyl singly substituted on the nitrogen atom with methyl.

5. A method in accordance with claim 1 wherein R is bromine, vinyl or methoxy and $n$ is 2 to 14.

6. A method in accordance with claim 5 wherein R is bromine and $n$ is 6 to 12.

7. A method in accordance with claim 6 wherein n is 9.

8. A method in accordance with claim 5 wherein R is methoxy and $n$ is 6 to 12.

9. A method in accordance with claim 8 wherein n is 9.

10. A method for inhibiting the normal growth pattern of insects which comprises contacting said insects with a metamorphosis-inhibiting amount of the compound of claim 1.

11. An insecticidal composition comprising a metamorphosis-inhibiting amount of the compound of claim 1 and an inert carrier.

12. An insecticidal composition comprising a metamorphosis inhibiting amount of the compound of claim 2 and an inert carrier.

13. An insecticidal composition comprising a metamorphosis inhibiting amount of the compound of claim 3 and an inert carrier.

14. An insecticidal composition comprising a metamorphosis inhibiting amount of the compound of claim 4 and an inert carrier.

15. An insecticidal composition comprising a metamorphorsis inhibiting amount of the compound of claim 5 and an inert carrier.

16. An insecticidal composition comprising a metamorphosis inhibiting amount of the compound of claim 6 and an inert carrier.

17. An insecticidal composition comprising a metamorphosis inhibiting amount of the compound of claim 7 and an inert carrier.

18. An insecticidal composition comprising a metamorphosis inhibiting amount of the compound of claim 8 and an inert carrier.

19. An insecticidal composition comprising a metamorphosis inhibiting amount of the compound of claim 9 and an inert carrier.

* * * * *